United States Patent [19]

Sugita et al.

[11] Patent Number: 5,112,944
[45] Date of Patent: May 12, 1992

[54] CYCLIC TETRAPEPTIDE AND PROCESS FOR PREPARING THE SAME

[75] Inventors: Kenji Sugita, Kobe; Hiroshi Itazaki, Takarazuka; Koichi Matsumoto, Toyonaka; Yoshimi Kawamura, Mino, all of Japan

[73] Assignee: Shionogi & Co., Ltd., Osaka, Japan

[21] Appl. No.: 536,764

[22] Filed: Jun. 12, 1990

[30] Foreign Application Priority Data

Jun. 30, 1989 [JP] Japan .................................. 1-170930

[51] Int. Cl.$^5$ .............................................. C07K 5/12
[52] U.S. Cl. .................................... 530/321; 435/71.1; 930/270; 930/DIG. 781
[58] Field of Search ................................ 530/317, 321

[56] References Cited

U.S. PATENT DOCUMENTS 4,737,487 4/1988 Watts et al. ........................... 530/328

OTHER PUBLICATIONS

Lehninger, Principles of Biochemistry, Worth Publishers, Inc., pp. 95-117 (1982).
"Studies on WF-3161. A New Antitumor Antibiotic", The Journal of Antibiotics, vol. 36 (1983), pp. 478-483, Kazuyoshi Umehara et al.

Primary Examiner—Christina Chan
Attorney, Agent, or Firm—Birch, Stewart, Kolasch & Birch

[57] ABSTRACT

A cyclic tetrapeptide having the formula (I):

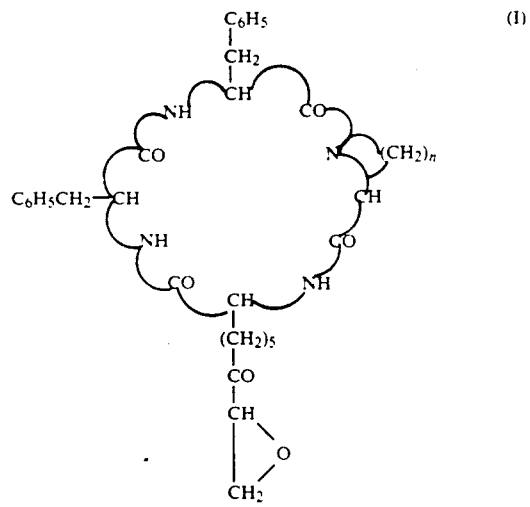

wherein n is 4 or 3 and a process for preparing the above cyclic tetrapeptide. The cyclic tetrapeptide of the present invention inhibits transformation of cells caused by oncogenes and possesses activities for recovering to a normal cell and for inhibiting proliferation of carcinoma cells. Therefore, the cyclic tetrapeptide of the present invention is useful for an active ingredient of an antitumor agent.

3 Claims, 8 Drawing Sheets

CYCLIC TETRAPEPTIDE AND PROCESS FOR PREPARING THE SAME

BACKGROUND OF THE INVENTION

The present invention relates to a novel cyclic tetrapeptide and a process for preparing the same.

The cyclic tetrapeptide according to the present invention is a novel compound which is not described in any literature or the like.

In The Journal of Antibiotics, 36, 478-483 (1983), compounds having similar structures to that of the compound of the present invention are listed. However, such compounds are distinguished from the compound of the present invention by their amino acid components. Also, there is no report which describes that such compounds inhibit transformation of cells.

With respect to a substance capable of normalizing transformed morphology of cells, there are reports as follows:

Genistein (Hiroshi Ogawara et al, The Journal of Antibiotics, 39, 606-608 (1986))

Erbstatin (Hamao Umezawa et al, The Journal of Antibiotics, 39, 170-173 (1986))

Oxanosine (Itoh, S. et al, Cancer Research, 49(4), 996-1000 (1989))

It is an object of the present invention to provide a cyclic tetrapeptide having the formula (I):

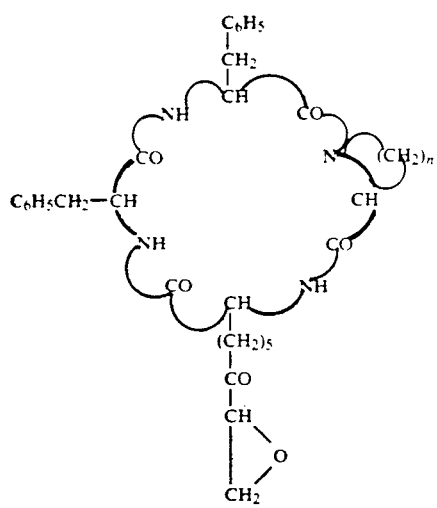

wherein n is 4 or 3. A further object of the present invention is to provide a process for preparing the cyclic tetrapeptide (I).

These and the other objects of the present invention will become apparent from the description hereinafter.

SUMMARY OF THE INVENTION

In recent years, it has been desired that a substance capable of reversibly converting the morphology of carcinoma cells to that of normal cells by inhibiting the action of oncogene products, and a process for preparing such substance, be developed.

As a result of the continuous effort of the present inventors, now it has been found that cyclic tetrapeptides obtained from cultures of *Helicoma ambiens* RF-1023, inhibit transformation of cells induced by oncogenes and possess excellent pharmacological characteristics which contain antitumor activities comprising an activity for returning transformed cells to normal cells and an activity for inhibiting cell proliferation of carcinoma cells. Consequently the present invention has been accomplished.

In accordance with the present invention, there is provided a cyclic tetrapeptide having the formula (I):

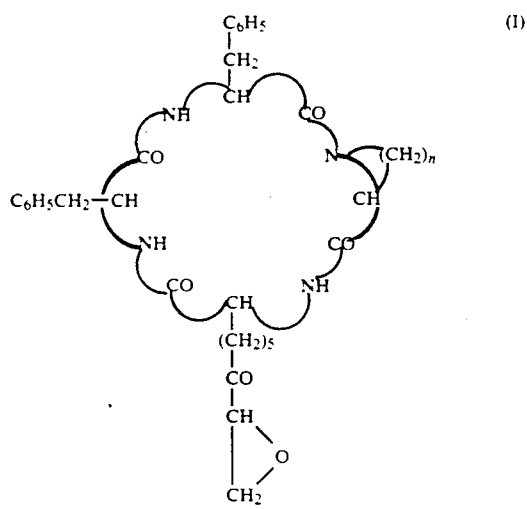

wherein n is 4 or 3.

The present invention also provides a process for preparing a cyclic tetrapeptide having the formula (I):

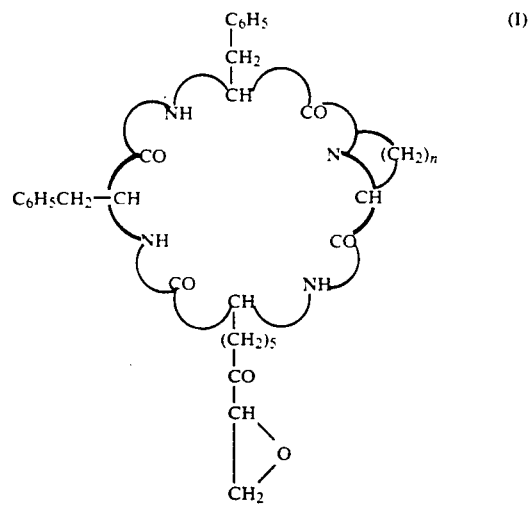

wherein n is the same as defined above, which comprises culturing a microorganism belonging to the genus Helicoma capable of producing a cyclic tetrapeptide having the formula (I) in a medium and collecting the produced cyclic tetrapeptide having the formula (I).

DETAILED DESCRIPTION

Figure 1:
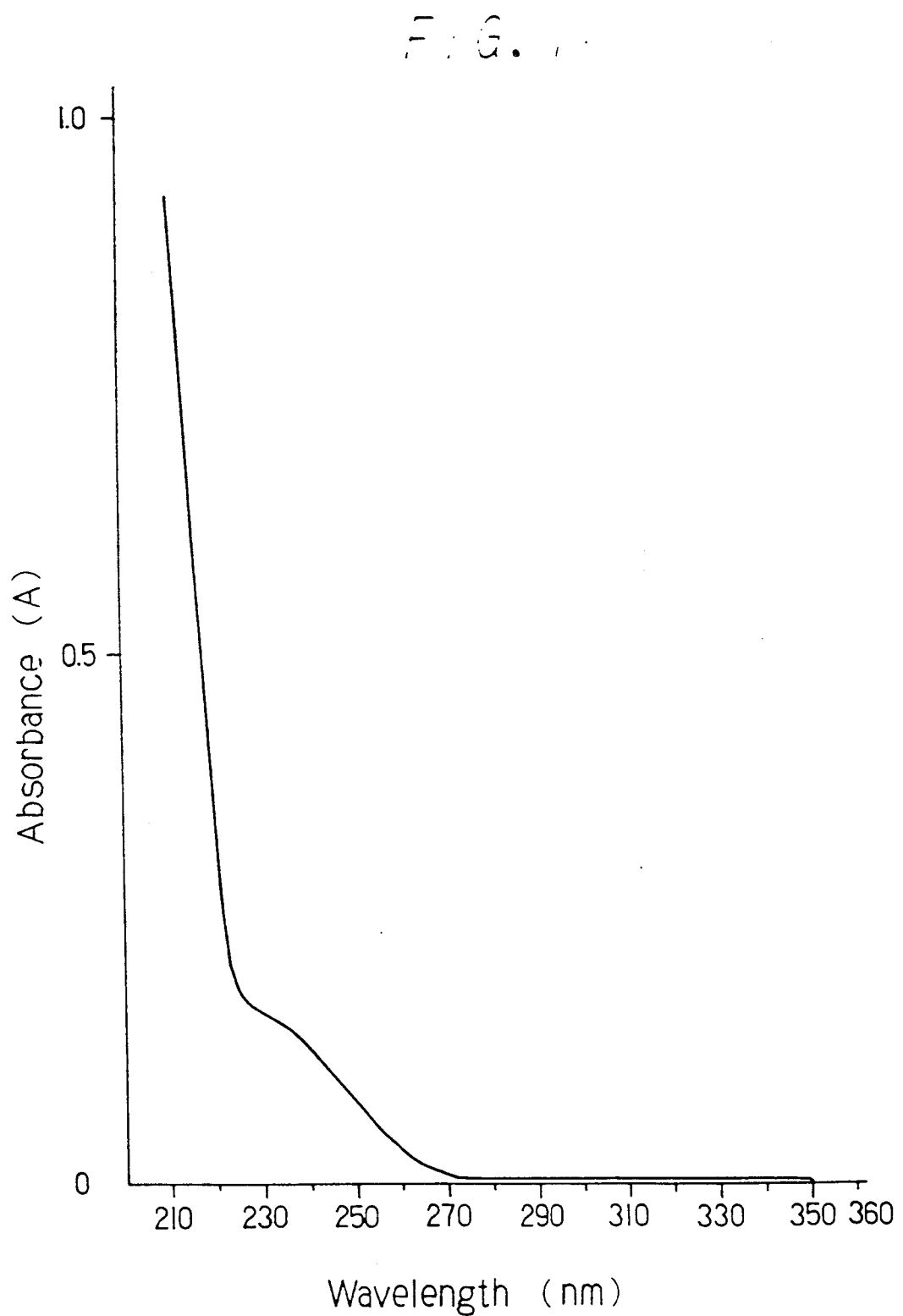
FIG. 1 is a chart showing UV absorption spectrum of RF-1023-A.

Microorganisms capable of producing the cyclic tetrapeptide having the formula (I) according to the process of the present invention can be found among those belonging to the genus Helicoma. Among them, *Helicoma ambiens* RF-1023 is exemplified as a typical strain.

Taxonomic studies of the strain RF-1023 are summarized as follows.

Colonies grow slowly on V8-juice agar. Condiophores are simple or little branced. The lower sterile part of the conidiophore is straight, and the upper fertile part is frequently geniculate and bent, mid-brown colored and very pale brown toward the tip, 65 to 270 μm in length and 3 to 4.5 μm in width. Conidia are 14 to 22 μm in diameter across the coil; the conidial filament is 5.5 to 9.0 μm at the widest part, 7 to 9-septate. Basal cell is U-shaped with an indistinct scar, pale olive to olive colored. Phoma state is not observed in the strain.

Based on the taxonomic properties described above, the strain RF-1023 was identified as *Helicoma ambiens* Morgan (1892) described by Pirozynsky, K. A. in Mycological papers, 129, 29–30 (1972). The strain RF-1023 which produces the cyclic tetrapeptide (I) of the present invention has been deposited in Fermentation Research Institute, Agency of Industrial Science and Technology, Japan under the accession number FERM BP-2751. The deposition date is April 21, 1989.

The mycological properties of the above-mentioned cyclic tetrapeptide (I)-producing microorganisms are apt to vary. All cyclic tetrapeptide having the formula (I)-producing microorganisms which belong to the genus Helicoma including natural variants as well as artificial variants can be employed in the present invention.

In case of preparing the cyclic tetrapeptide having the formula (I) of the present invention, first the cyclic tetrapeptide having the formula (I)-producing microorganisms belonging to the genus Helicoma are inoculated in a nutrient medium for the inducing of the cyclic tetrapeptide (I), cultivation is aerobically carried out, and the desired cyclic tetrapeptide having the formula (I) is obtained.

As cultivation, for instance, the following methods are exemplified.

First, the cyclic tetrapeptide (I)-producing cells are inoculated in a medium and cultured.

As a nutrient medium used in such cultivation, a medium to which an organic nitrogen source such as polypeptone (made by Nippon Seiyaku Co., Ltd.), beef extract (made by Difco), yeast extract (made by Difco), malt extract (made by Difco) or BACTOPEPTONE (made by Difco), a carbon source such as glucose, soluble starch or potato starch, an inorganic salt such as NaCl are added, is usually employed. For cultivation, shaking culture is preferable.

In such shaking culture, the number of shaking times is preferably 180 rpm, more preferably 120 rpm.

Temperature of culture is preferably 25° to 30° C., more preferably 27° to 28° C. Time of culture is preferably 48 to 96 hours, more preferably 72 hours.

Then, the culture solution obtained by the above-mentioned culture is inoculated in a fresh medium and cultured.

In the present invention, constitution of medium, medium conditions and the like usually used in production of antibiotics are used. In principle the medium contains a carbon source, nitrogen source, inorganic salts and the like. As occasion demands, vitamins, precursors, for instance, phenylacetic acid or amino acids such as phenylalanine and other additives, can be added. Examples of the carbon sources are, for instance, potato decoction, potato starch, sucrose, soluble starch, glucose, corn starch, dextrin, glycerin, treacle, organic acids and the like. They may be used alone or as an admixture thereof. Examples of the nitrogen sources are, for instance, soybean meal, corn steep liquor, meat extract, yeast extract (made by Difco), cotton seed meal, peptone, polypeptone (made by Nippon Seiyaku Co., Ltd), wheat germ, ammonium sulphate, ammonium nitrate, malt extract (made by Difco) and the like. They may be used alone or as an admixture thereof. Examples of the inorganic salts are, for instance, calcium carbonate, sodium chloride, potassium chloride, magnesium sulfate, copper sulfate, manganese chloride, zinc sulfate, cobalt chloride, various phosphates and the like. They are added to a medium as occasion demands.

Culture may be carried out according to a method usually used in production of antibiotics. A liquid culture is preferred. In case of carrying out mass production, a submerged culture is preferred. When it is possible that pH of a medium varies, buffer such as calcium carbonate may be added in the medium. In case of furious effervescence during the culture, preferably an antifoaming agent, for instance, such as vegetable oil, lard or polypropylene glycol is suitably added to a medium before or during the culture. For cultivation, shaking culture is preferable.

In such shaking culture, the number of shaking times is preferably 120 to 180 rpm, more preferably 180 rpm (7 cm stroke). Temperature of culture is preferably 25° to 30° C., more preferably 27° to 28° C. Time of culture is preferably 10 to 14 days, more preferably 12 to 14 days.

The cyclic tetrapeptide having the formula (I) of the present invention can be obtained according to, e.g., the following method.

The obtained culture solution is filtered according to conventional method to separate cells and filtrate. The obtained microorganisms are extracted with an organic solvent such as methanol, acetone or ethanol. Then the extract is concentrated. After the pH is adjusted to 1.0–5.0, the concentrate is extracted with an organic solvent such as ethyl acetate, butanol or methylene chloride; thereafter, the crude extract (1) is obtained via a conventional purification operation.

Meantime, after the pH of the above-mentioned filtrate is adjusted to 1.0–5.0, the filtrate is extracted with an organic solvent such as ethyl acetate, butanol or methylene chloride; thereafter the crude extract (2) is obtained via conventional operation.

The above-mentioned crude extracts (1) and (2) are mixed. The mixed sample is isolated and purified by means of thin layer chromatography for preparation (hereinafter referred to as "TLC"), and then recrystallized. The desired cyclic tetrapeptide having the formula (I) can be obtained.

In the above-mentioned TLC, MERCK PRE-COATED TLC PLATE SILICA GEL 60 F-254 and the like as a plate for TLC, and the mixed solvent of toluene: ethyl acetate (1:1) and the like as a developing solvent, are preferable.

Besides, as a means for detection, the cyclic tetrapeptide having the formula (I) can be directly non-destructively detected under ultraviolet light after developing TLC when a plate is employed on which fluorescent dye is mixed.

On the plate for TLC adjacent two bands are observed (hereinafter referred to as "band I" and "band II").

RF-1023-A having the formula (I) wherein $n=4$ is obtained from the obtained band I, and a mixture of RF-1023-A and RF-1023-B having the formula (I) wherein $n=3$ is obtained from the obtained band II. Separation of RF-1023-B from band II is carried out by means of TLC.

The above-mentioned MERCK PRE-COATED TLC PLATE and the like as a plate for the TLC and the mixed solvent of methylene chloride: methanol (9:1) and the like as a developing solvent are preferable. Besides, as a means for detection, the cyclic tetrapeptide having the formula (I) can be directly non-destructively detected under ultraviolet light after developing TLC when a plate is employed on which fluorescent dye is mixed. Also, RF-1023-B having the formula (I) wherein $n=3$ can be obtained by the above-mentioned TLC. The obtained RF-1023-A and RF-1023-B may be further purified by recrystallization and the like according to conventional methods.

Antitumor agents containing the cyclic tetrapeptide having the formula (I) of the present invention as an effective ingredient can be in any preparation form for oral or parenteral administration. Examples of the preparation form are, for instance, preparations for oral administration such as tablets, capsules, granules and syrups, and preparations for parenteral administration such as suppositories, ointments and injections. Carriers used for the preparation of the antitumor agents according to the present invention are organic or inorganic pharmaceutical carriers in either solid or liquid state, which are inactive under usual conditions, suitable for oral or parenteral administration. Examples of carriers for oral administration are, for instance, starch, mannitol, crystalline cellulose, water, ethanol and the like. Examples of carriers for parenteral administration are, for instance, water, normal saline, a glucose solution and the like. The ratio of the antitumor agent of the present invention to the carrier in the preparation can vary from 1 to 99% by weight. Also, the antitumor agents according to the present invention can contain another pharmaceutical ingredient such as another antitumor agent compatible with the cyclic tetrapeptide of the present invention. In this case, the antitumor agent according to the present invention is not necessarily a main ingredient of the preparation.

The compound and the process for preparing thereof of the present invention are more particularly described and explained by means of the following Examples and Test Examples in which all percents and parts are by weight unless otherwise noted. It is to be understood, however, that the present invention is not limited to the Examples, the Test Examples and various changes and modifications can be made without departing from the spirit and scope of the present invention.

EXAMPLE 1

A slant culture of the strain RF-1023 (FERM BP-2751) was inoculated into 100 ml of a seed medium containing 1.0% polypeptone, 2.0% glucose, 0.3% beef extract, 0.2% yeast extract, 0.1% NaC: and tap water (pH 7.0) in a 500-ml SAKAGUCHI flask, and cultured at 28° C. on a rotary shaker at 120 rpm (7 cm stroke) for 72 hours. The seed culture was then transferred at the rate of 4 ml to 80 ml of a production medium which contained 2.0% potato starch, 2.0% sucrose and 0.5% yeast extract (pH 7.0) and was placed in each of twenty four 500-ml ERLENMEYER flasks and cultivation was carried out for 12 days at 28° C. under shaking at 180 rpm.

Two l of the obtained culture solution was filtered by means of a HYFRO SUPER-CELL (made by JOHNS-Manville Sales. Corp.) to separate cells and filtrate.

To 2 l flask was added the obtained cells and then was added 500 m: of methanol. On a magnetic stirrer, homogenization was carried out for 10 minutes. Subsequently the resulting solution was filtered off. After concentrating the filtrate at 30° to 40° C. by a rotary evaporator on water bath, thereto was added 2N hydrochloric acid solution to adjust the pH to 2.0. The resulting solution was extracted with 100 ml of ethyl acetate twice, and then was washed with water. The washed solution was dried with $Na_2SO_4$ to give 240 mg of the crude extract (1).

On the other hand, the filtrate (pH 6.7) obtained from the filtration of the culture solution was transfered into a 4 l vessel. Thereto was added 2N hydrochloric acid solution to adjust the pH to 2.0. The resulting solution was extracted with 600 ml of ethyl acetate twice, and then was washed with 20% aqueous solution of NaCl. The washed solution was dried with $Na_2SO_4$ to give 317 mg of the crude extract (2).

The obtained crude extracts (1) and (2) (total 557 mg) were dissolved in ethyl acetate. The resulting solution was separated by means of TLC (plate for TLC: 20×20 cm MERCK PRE-COATED TLC PLATE SILICA GEL 60 F-254 (made by Merck & CO. INC., developing agent: toluene-ethyl acetate (1/1: v/v) and detection method: direct detection under ultraviolet light after developing) to give adjacent two bands on the plate for TLC (hereinafter referred to as "band I" and "band II").

From the obtained band I was recovered 190 mg of RF-1023-A. In addition, from the band II being the mixed band of RF-1023-A and RF-1023-B was recovered 55 mg of RF-1023-A. The separation of RF-1023-A from band II was carried out by dissolving the total 173 mg of RF-1023-A and RF-1023-B in ethyl acetate and subjecting the solution to TLC (plate for TLC: 20×20 cm, MERCK PRE-COATED TLC PLATE SILICA GEL 60 F-254 (made by Merck & CO. INC.), developing solvent: $CH_2Cl_2$-methanol (9/1: v/v) and detection method: direct detection under ultraviolet light after developing).

Further 245 mg of the obtained RF-1023-A was dissolved in 10 ml of isopropyl alcohol at 55° C., and then 0.2 ml of water was added thereto. The solution was recrystallized to give 184 mg of the desired cyclic tetrapeptide RF-1023-A (colorless, needls). Hereinafter, the physicochemical properties of the compound RF-1023-A of the present invention are shown.

Physicochemical properties;

Melting point: 173°-174° C. (recrystallization from propanol-water).

Color reaction: negative; Ninhydrin reagent; positive; Dragendolff reagent; $H_2SO_4$-heat; phosphomolybdic acid reagent.

UV absorption spectrum (FIG. 1) MeOH $\lambda_{max}$ nm($E_{lcm}^{1\%}$) end absorption, 235(sh) (75).

Figure 2:
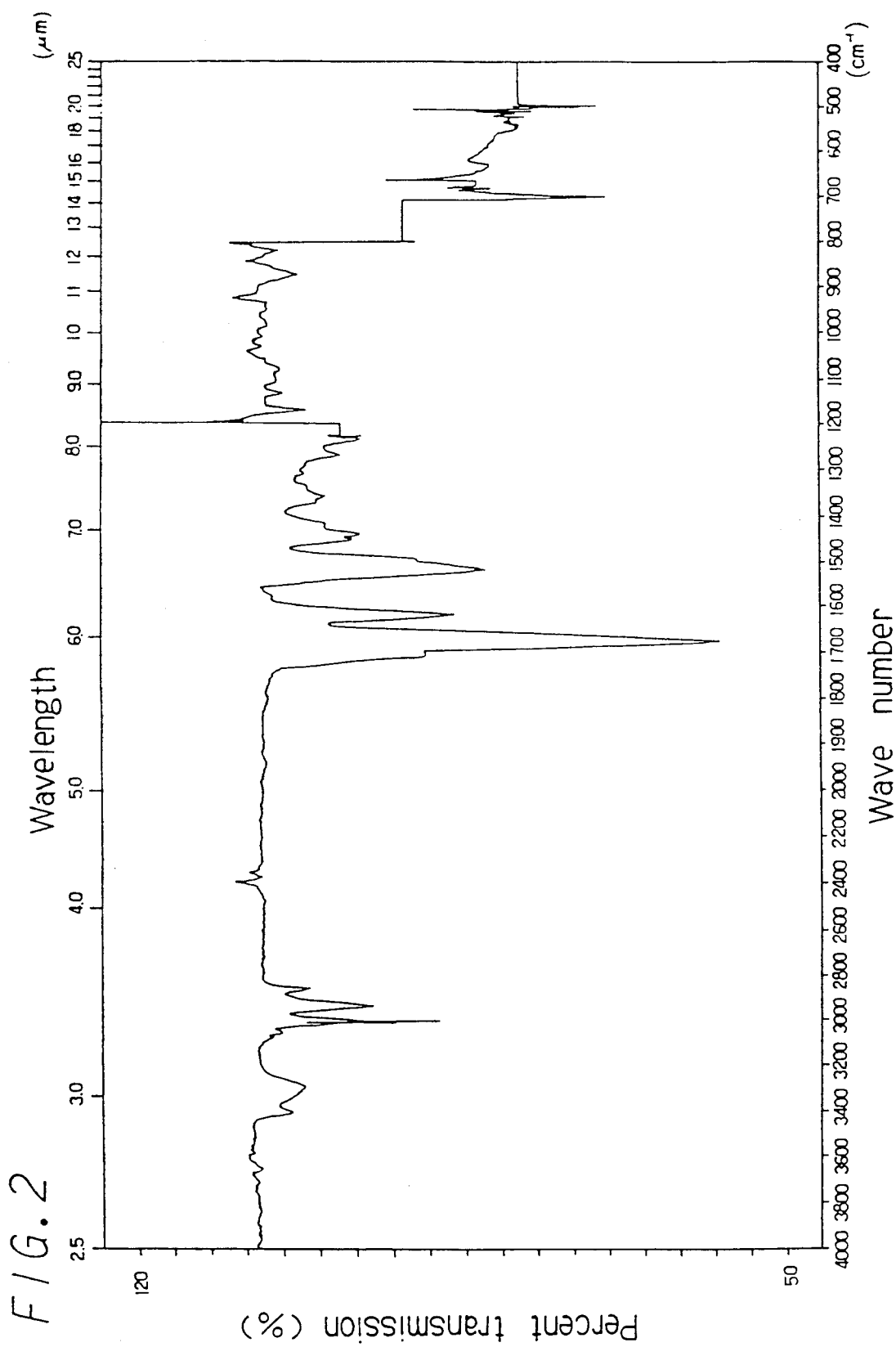
FIG. 2 is a chart showing IR absorption spectrum of RF-1023-A.

IR absorption spectrum (FIG. 2)

IR(Chf) cm$^{-1}$: 3410, 3296, 3022, 2930, 2858, 1710, 1680, 1622, 1522, 1440, 1360, 1270, 1231, 1170, 1133, 1082, 874.

Specific rotation $[\alpha]_D^{24}$: $-63.7\pm2.0°$ (c=0.515, MeOH).

Mass spectrography

SIMS: 603[M+H]$^+$ (calculated value of $C_{34}H_{42}O_6N_4$+H).

Elementary analysis (for $C_{34}H_{42}O_6N_4+0.2H_2O$). calculated (%): C:67.35, H:7.05, N:9.24, found (%) : C:67.40, H:7.13, N:9.42, Amino acid analysis L-phenylalanine (2), D-pipecolinic acid (1) (Configuration of amino acid (i.e. D-form or L-form) was determined by optical active column {phenylalanine: CROWNPAK CR (DAICEL CHEMICAL INDUSTRIES, LTD.), solvent: 1 % HClO$_4$, flow rate: 0.8 ml/min, pipecolinic acid: TSKGEL ENANTIO L1 (TOSOH CORPORATION), solvent: 0.25 mmol, flow rate: 1.0 ml/min}.)

Figure 3:
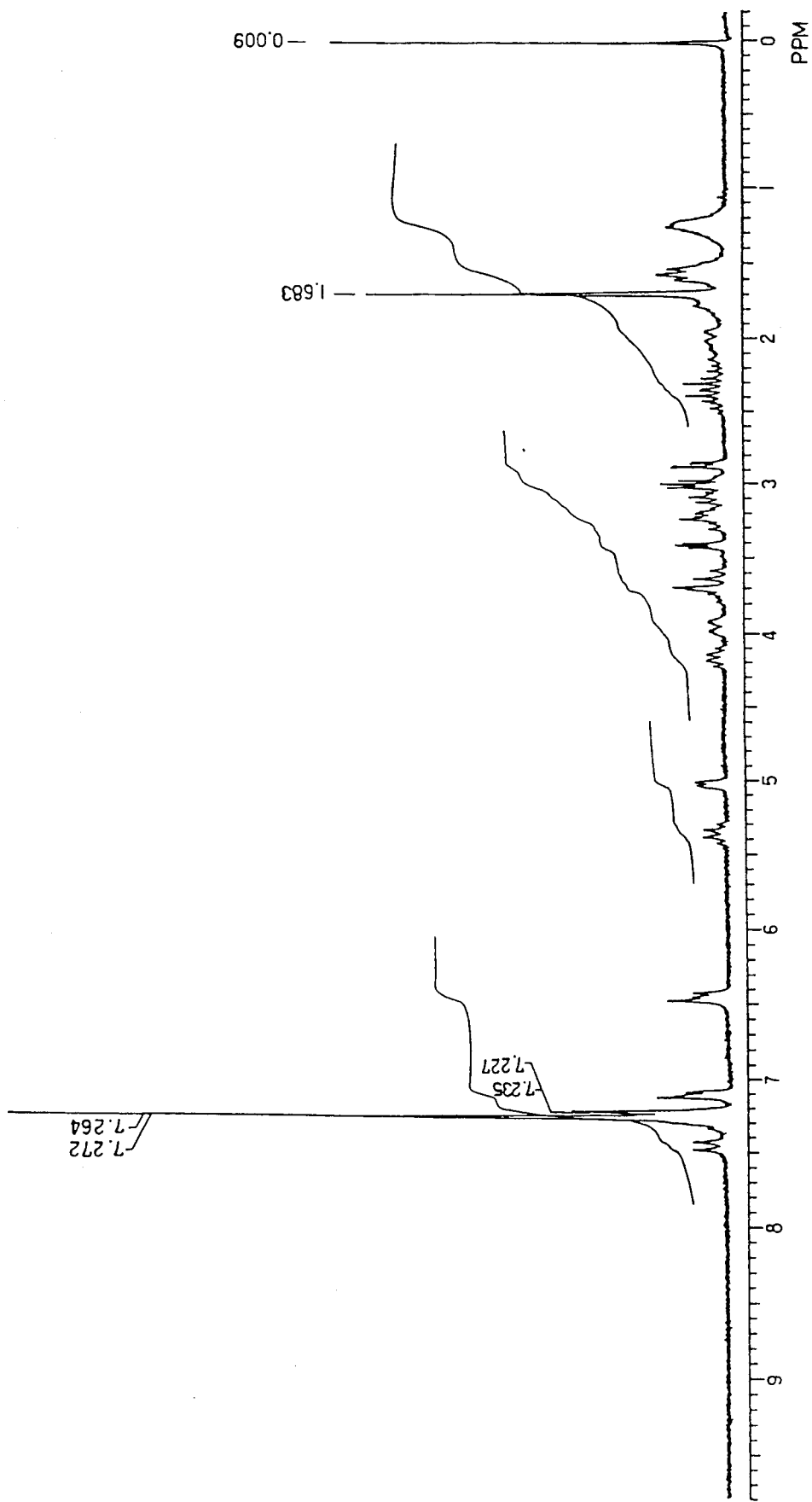
FIG. 3 is a chart showing NMR spectrum ($^1$H—NMR) of RF-1023-A.

NMR spectrum $^1$H-NMR[200MHz, CDCl$_3$ (internal standard TMS)], ppm(J=Hz) (FIG. 3) 7.46(1H, d, J=10), 7.27(10H, s), ca. 7.11(1H,m), ca. 6.46(2H, m), 5.36(1H, q, J=9), 5.02(1H, d, J=5), 4.17(1H, q, J=9), 3.96(1H, d, J=9), 3.43 (1H, d of d, J=6, 1.4), 3.00(1H, t, J=6), 2.86(1H, d of d, J=6, 1.4), 4.20-2.80(m), 2.50-1.70(m), 1.56(2H, t), 1.46 (2H, br).

Figure 4:
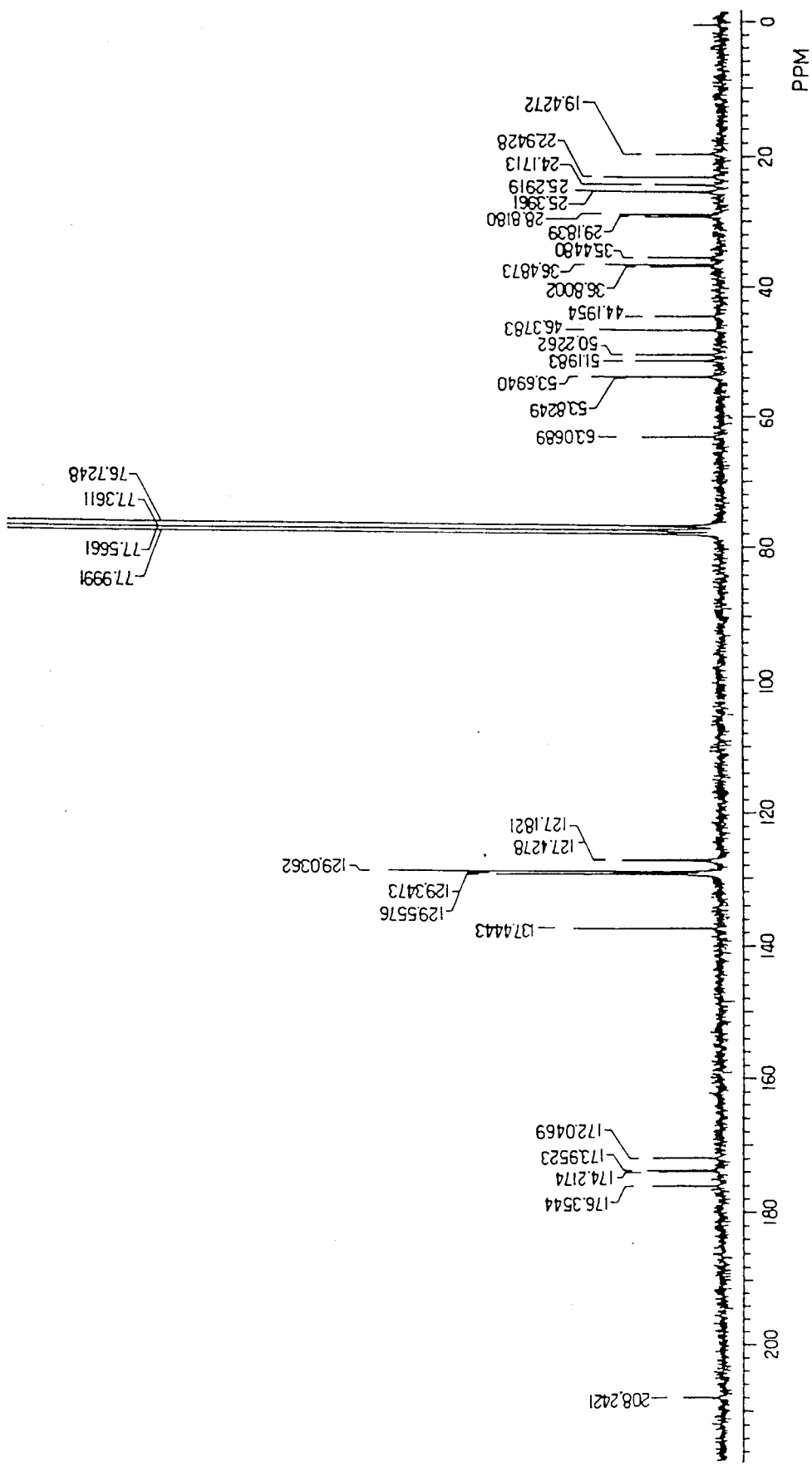
FIG. 4 is a chart showing NMR spectrum ($^{13}$C—NMR) of RF-1023-A.

$^{13}$C—NMR[50 MHz, CDCl$_3$ (internal standard TMS)], ppm (FIG. 4) 19.43(t), 22.92(t), 24.17(t), 25.29(t), 25.40(t), 28.82(t), 29.18(t), 35.45(t), 36.49(t), 36.80(t), 44.20(t), 46.38(t), 50.23(d), 51.20(d), 53.69(d), 53.82(d), 63.07(d), 127.18(d), 127.43(d), 129.04(d×4), 129.35(d×2), 129.56(d×2), 137.44(d×2), 127.05(s), 173.95(s), 174.22(s), 176.35(s), 208.24(s).

The stereochemical structure of the compound RF-1023-A of the present invention is shown as follows:

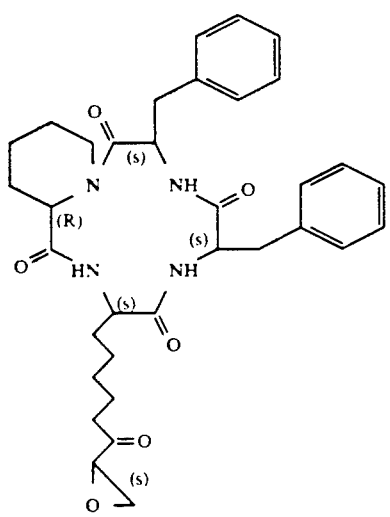

RF-1023-A

EXAMPLE 2

In the same manner described in Example 1, the procedure was carried out to give 72 mg of RF-1023-B from the band II being the mixed band of RF-1023-A and RF-1023-B.

To 1 ml of methanol was added 72 mg of the obtained RF-1023-B. The RF-1023-B was recrystallized to give 72 mg of the desired cyclic tetrapeptide RF-1023-B (colorless, needls).

The physicochemical properties of the compound RF-1023-of the present invention are shown as follows.

Physicochemical properties;

Melting point: 188°190° C. (recrystallization from methanol-water).

Color reaction: negative; Ninhydrin reagent; positive; Dragendolff reagent; $H_2SO_4$-heat. phosphomolybdic acid reagent.

Figure 5:
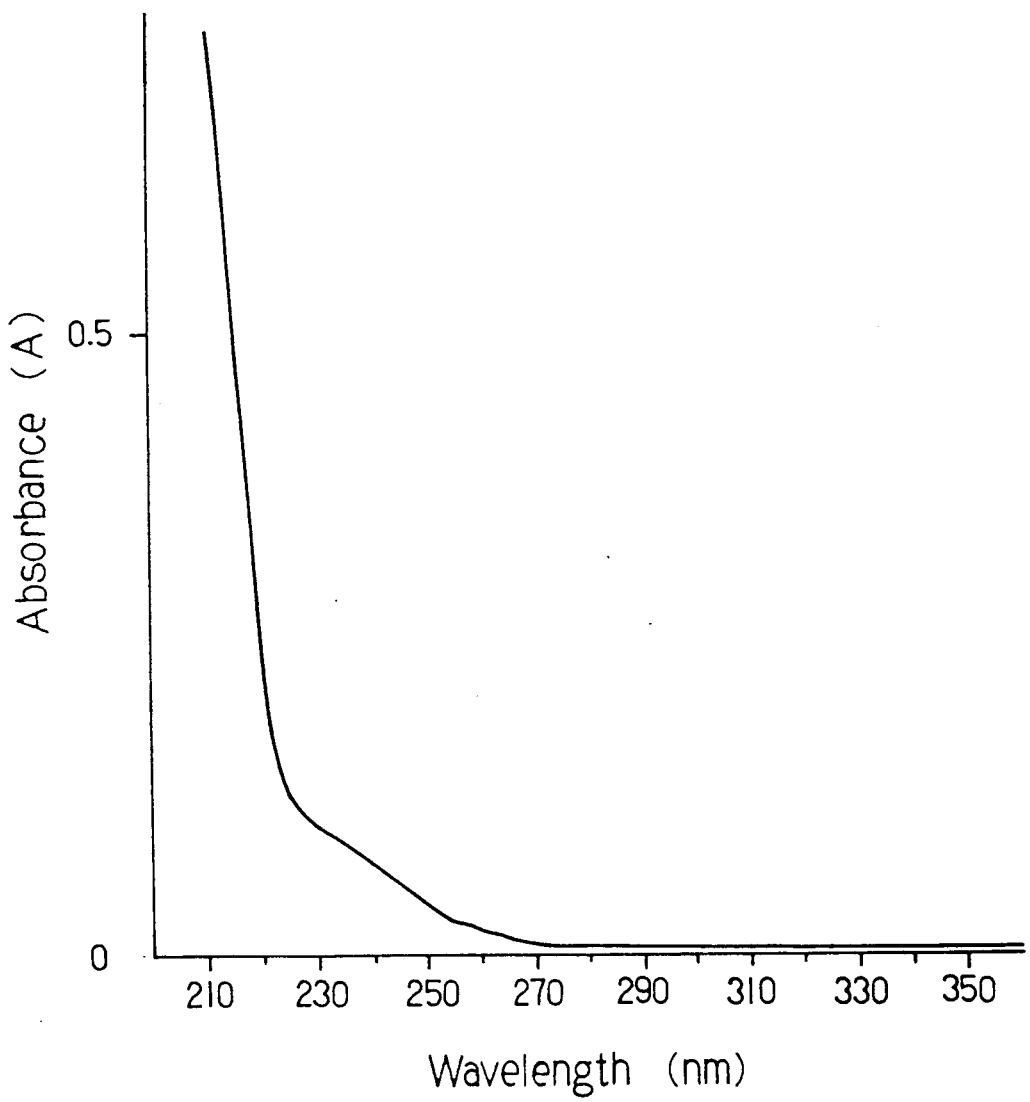
FIG. 5 is a chart showing UV absorption spectrum of RF-1023-B.

UV absorption spectrum (FIG. 5) MeOH 1% $\lambda_{max}$ nm($E_{lcm}^{1\%}$) end absorption, 235(sh) (90).

Figure 6:
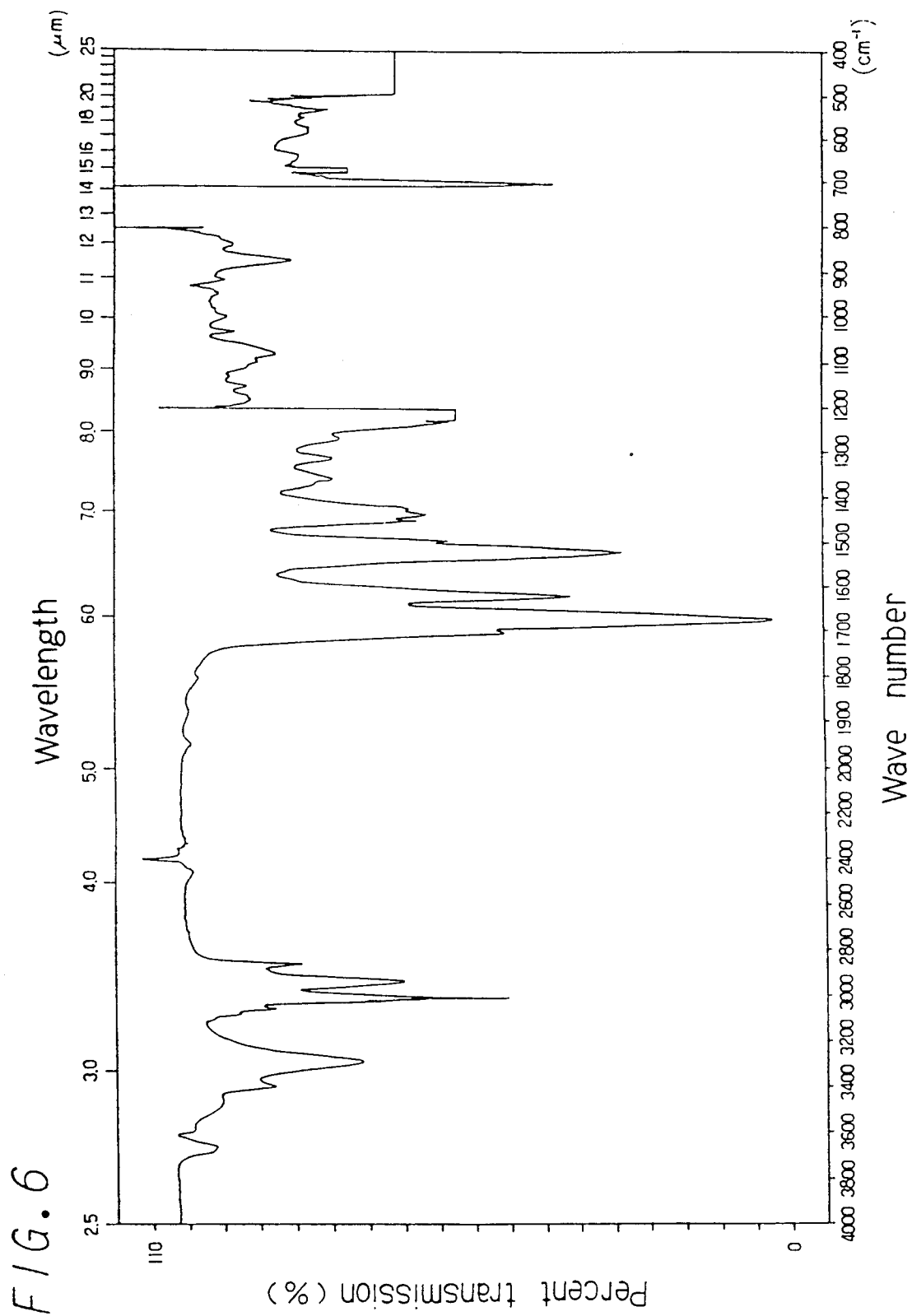
FIG. 6 is a chart showing IR absorption spectrum of RF-1023-B.

IR absorption spectrum (FIG. 6)

IR(Chf) cm$^{-1}$: 3402, 3292, 3008, 2934, 2856, 1706, 1678, 1622, 1521, 1437, 1358, 1312, 1267, 1077, 872.

Specific rotation $[\alpha]_D^{24}$: $-75.3\pm2.2°$ (c=0.517, MeOH).

Mass spectrography

SIMS: 589[M+H]$^+$ (calculated value of $C_{33}H_{40}O_6N_4$+H).

Elementary analysis (for $C_{33}H_{40}O_6N_4+0.5H_2O$). calculated (%): C:66.31, H:6.91, N:9.37. found (%) : C:66.00, H:6.78, N:9.40.

Amino acid analysis

L-phenylalanine (2), D-proline (1) (Configuration of amino acid (i.e. D-form or L-form) was determined by optical active column {phenylalanine: CROWNPAK CR (DAICEL CHEMICAL INDUSTRIES, LTD.), solvent: 1 % HClO$_4$, flow rate: 0.8 ml/min., proline: TSKGEL ENANTIO L1 (TOSOH CORPORATION), solvent: 0.25 mmol, flow rate: 1.0 ml/min}.)

Figure 7:
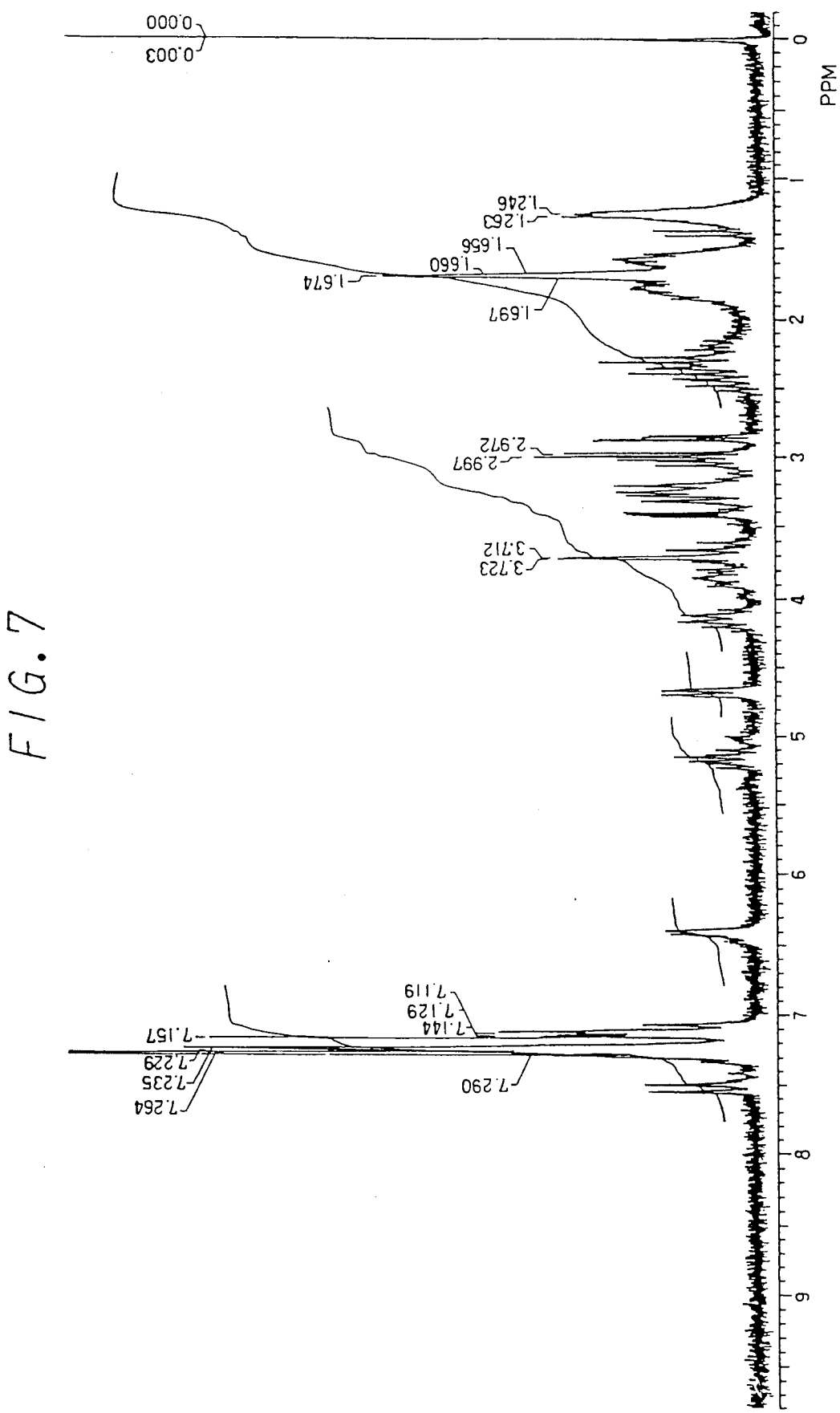
FIG. 7 is a chart showing NMR spectrum ($^1$H—NMR) of RF-1023-B.

NMR spectrum $^1$H—NMR[200MHz, CDCl$_3$(internal standard TMS)], ppm(J32 Hz) (FIG. 7) 7.65(1H, d, J=10), 7.13(2H, m), ca. 6.40(1H, br), 7.29-7.23(10H, m), 5.18(1H, m), 4.68(1H, d, J=5), 4.15(1H, m), 3.85(1H, m), ca. 3.72(1H, m), 3.42(1H, d of d, J=6, 1.4), 3.00(1H, t, J=6), 2.86(1H, d of d, J=6, 1.4), 2.50-1.20(m)

Figure 8:
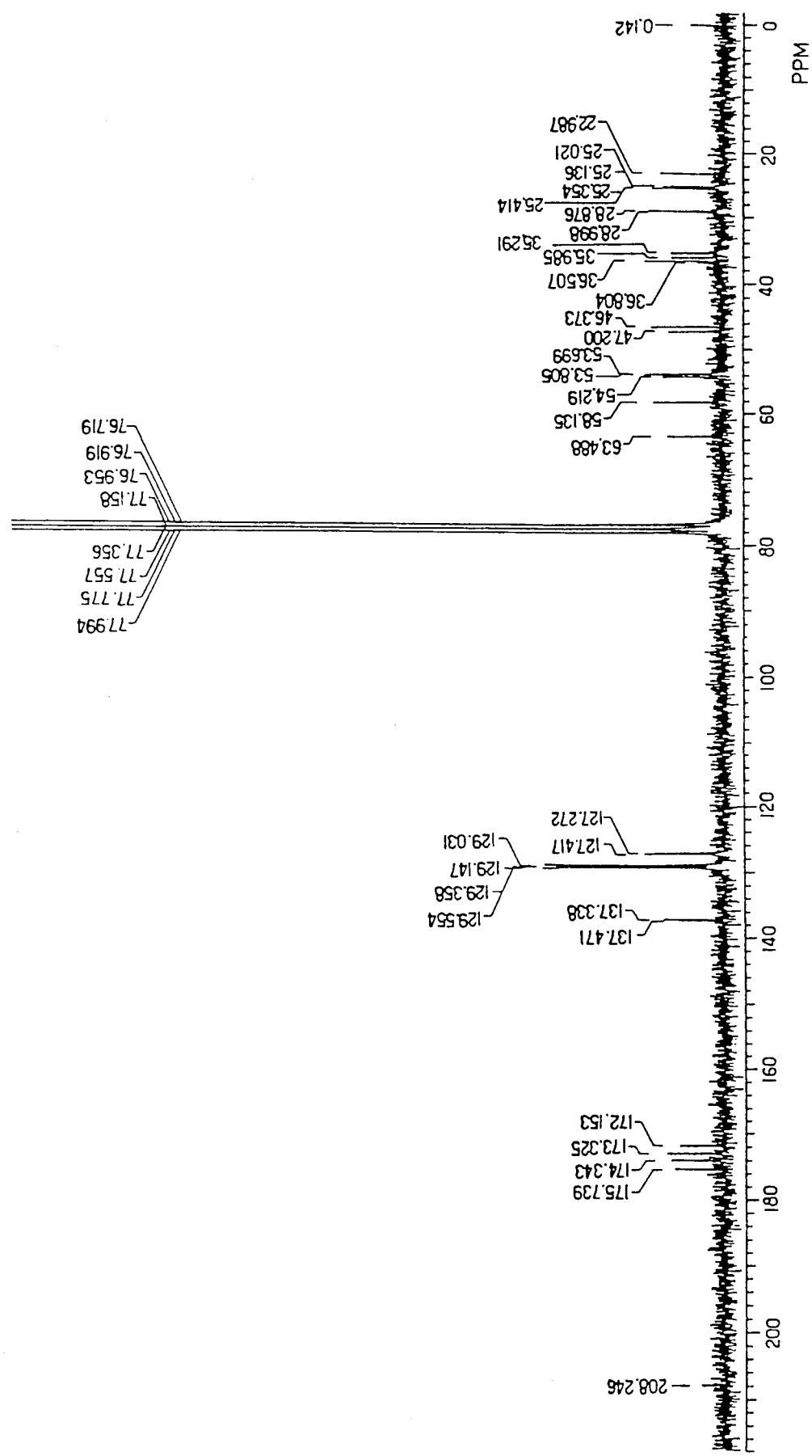
FIG. 8 is a chart showing NMR spectrum ($^{13}$C—NMR) RF-1023-B.

$^{13}$C-NMR[50 MHz, CDCl$_3$ (internal standard TMS)], ppm (FIG. 8) 22.99(t), 25.02(t), 25.14(t), 25.41(t), 28.88(t), 29.00(t), 35.29(t), 35.99(t), 36.51(t), 46.37(t), 47.20(t), 53.70(d), 35.81(d), 54.22(d), 58.15(d), 63.49(d), 127.27(d), 127.42(d), 129.03(d×2), 129.15(d×2), 129.36(d×2), 129.55(d×2), 137.34(d), 137.47(s), 172.15(s), 173.33(s), 174.34(s), 175.74(s), 208.25(s)

The stereochemical structure of the compound RF-1023-B of the present invention is shown as follows:

RF-1023-B

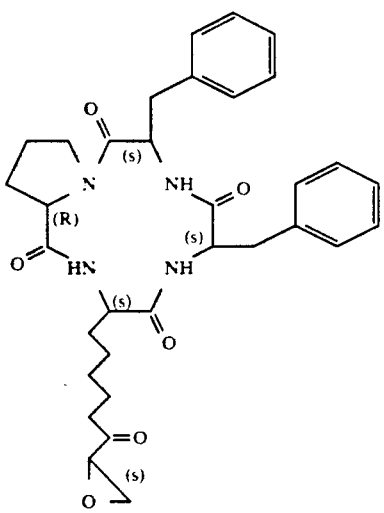

TEST EXAMPLE 1

(Experimental method)

The employed culture solution was prepared by adding 9.5 g of DALBECCO'S EAGLE MEM medium (made by NISSUI SEIYAKU CO., LTD.) and 20 ml of 7% sodium bicarbonate to 1 l of distilled water and then adding fetal bovine serum (made by Flow Laboratories, Inc., U.S.A.) to be 10% by volume at the final concentration.

To each well of a 12-well plastic dish made by Flow Laboratories, Inc., 2 ml of the above-mentioned culture solution, $2 \times 10^4$ cells/ml of NIH3T3 cells transformed with sis oncogene (provided by National Cancer Institute of the U.S.; Science, 218, 1131 (1982)) and each test compound (RF-1023-A or RF-1023-B) in each concentration (5 to 400 ng/ml) were added and cultured at 37° C. in 5% $CO_2$ incubator. Twenty-four hours later the morphology of the cells was observed and detransformation activity (activity for inhibiting transformation of NIH3T3 cells transformed with the oncogene and returning to normal flat morphology of cells) was estimated. Two days after the incubation, cells subjected to the medium containing RF-1023-A were dispersed with 0.05% trypsin, and the cell number was measured by means of hemocytometer.

Results of the test

As is clear from Table 1, the compound of the present invention shows detransformation activity at the concentration of 5 ng/ml. In the same experiment system, hexamethylene bisacetamide (HMBA), reported as a differentiation-inducing agent, shows detransformation activity at the concentration of 3 mg/ml. Therefore, the activity of the compound of the present invention is remarkably high in comparison with HMBA. Also, both RF-1023-A and RF-1023-B gave the same result.

From Table 2, the compound of the present invention shows a cytostatic effect in the concentration not less than 5 ng/ml, and completely inhibits cell proliferation in the concentration not less than 100 ng/ml.

TABLE 1

| Concentration of the test compound (ng/ml) | Detransformation activity[*1] |
|---|---|
| 0 | − |
| 5 | + |
| 50 | + |
| 100 | + |
| 200 | + |
| 400 | + |

(Note)
[*1] "+" means that morphology of cells not less than 75% were flat in the judgment of 24 hours after the incubation.

TABLE 2

| Concentration of the test compound (ng/ml) | Cell number[*2] | Percentage of increase (%) |
|---|---|---|
| 0 | $8.0 \times 10^5$ | 100 |
| 5 | $3.8 \times 10^5$ | 35 |
| 50 | $3.4 \times 10^5$ | 29 |
| 100 | $1.5 \times 10^5$ | 0 |
| 200 | $1.1 \times 10^5$ | −6 |
| 400 | $1.1 \times 10^5$ | −6 |

(Note)
[*2] Cell numbers were measured at 2 days after the incubation.

TEST EXAMPLE 2

Experimental method

After collecting by syringe (made by TERUMO CORPORATION), human red blood cells were precipitated by centrifuging at 1500 rpum for 15 minutes, and $3 \times 10^8$ cells/ml suspension of human red blood cells was prepared with MEM medium containing fetal bovain serum to give a final concentration of 10% by volume.

Equivalent of the obtained human red blood cell suspension and a diluted solution (1 to 50 μg/ml) of the test compound of the present invention (RF-1023-A or RF-1023-B) were mixed and cultured at 37° C. in a 5 % $CO_2$ incubator for 2 days. After centrifuging at 1500 rpm, the amount of hemoglobin in the supernatant was assayed by measuring the absorption at 538 nm by Auto reader (made by Dynatech Co. & Ltd, U.S.A.).

Results of experiment

The compound of the present invention did not show a hemolysis effect at all at the concentration of 25 μg/ml against human red blood cells.

According to the above-mentioned experiments, the compound of the present invention inhibits the transforming of NIH3T3 cells transformed with the oncogene, has activity for returning to flat morphology of cells (detransformation activity), and also has a cytostatic effect against the transformed NIH3T3 cells.

In addition to the ingredients used in the Examples, other ingredients can be used in the Examples as set forth in the specification to obtain substantially the same results.

What is claimed is:

1. A cyclic tetrapeptide having the formula (I):

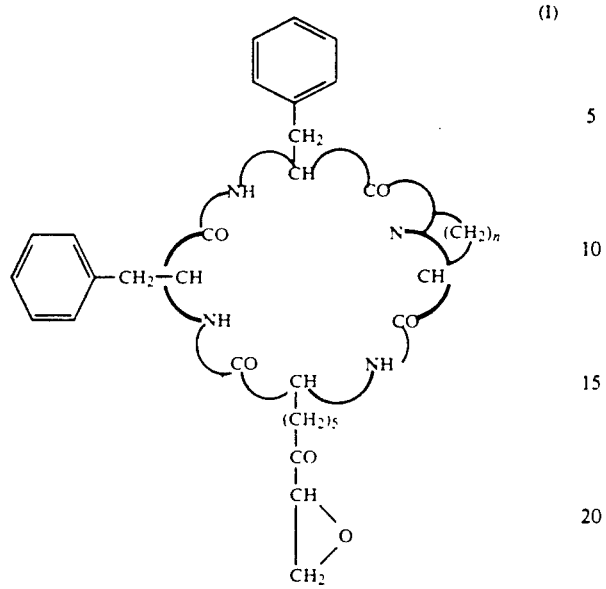
(I)
wherein n is 4 or 3.
2. The cyclic tetrapeptide of claim 1, wherein n is 4.
3. The cyclic tetrapeptide of claim 1, wherein n is 3.
* * * * *